US00PP23337P3

(12) United States Plant Patent
Cummins et al.

(10) Patent No.: US PP23,337 P3
(45) Date of Patent: Jan. 22, 2013

(54) APPLE TREE ROOTSTOCK NAMED 'G.210'

(50) Latin Name: ***Malus domestica×Malus robusta* hybrid**
Varietal Denomination: G.210

(75) Inventors: James Cummins, Geneva, NY (US); Herbert Sanders Aldwinckle, Geneva, NY (US); Terence Lee Robinson, Geneva, NY (US); Gennaro Fazio, Geneva, NY (US)

(73) Assignees: Cornell University, Ithaca, NY (US); The United States of America as Represented by the Secretary of Agriculture, Washington, DC (US)

( * ) Notice: Subject to any disclaimer, the term of this patent is extended or adjusted under 35 U.S.C. 154(b) by 31 days.

(21) Appl. No.: 12/931,756

(22) Filed: Feb. 9, 2011

(65) Prior Publication Data

US 2012/0204299 P1 Aug. 9, 2012

(51) Int. Cl.
*A01H 5/00* (2006.01)

(52) U.S. Cl. ..... Plt./174

(58) Field of Classification Search ..... Plt./174
See application file for complete search history.

(56) References Cited

U.S. PATENT DOCUMENTS

| | | | | |
|---|---|---|---|---|
| PP4,678 | P | 3/1981 | Carlson | |
| PP7,714 | P | 11/1991 | Masseron et al. | |
| PP7,715 | P | 11/1991 | Masseron et al. | |
| PP8,543 | P | 1/1994 | Cummins et al. | |
| PP11,070 | P | 9/1999 | Cummins et al. | |
| PP12,443 | P2 | 3/2002 | Cummins et al. | |
| PP17,063 | P3 * | 8/2006 | Cummins et al. | Plt./174 |
| PP18,618 | P2 | 3/2008 | Alston | |
| PP21,223 | P3 | 8/2010 | Budagovsky | |
| 2002/0002717 | P1 | 1/2002 | Yoshida et al. | |
| 2006/0130195 | P1 | 6/2006 | Cummins et al. | |
| 2006/0174386 | P1 | 8/2006 | Cummins et al. | |
| 2006/0174387 | P1 | 8/2006 | Cummins et al. | |
| 2010/0132081 | P1 | 5/2010 | Budagovsky et al. | |
| 2012/0096609 | P1 * | 4/2012 | Cummins et al. | Plt./161 |

* cited by examiner

*Primary Examiner* — Susan McCormick Ewoldt
(74) *Attorney, Agent, or Firm* — MacMillan, Sobanski & Todd, LLC

(57) ABSTRACT

A new and distinct variety of apple tree rootstock *Malus domestica×Malus robusta* hybrid 'G.210' is described herein. The new variety is a semi-dwarfing rootstock that is resistant to fire blight (*Erwinia amylovora*) and crown rot (*Phytophthora cactorum*). The 'G.210' rootstock is useful in that it can be propagated clonally and used as a rootstock or root system for apple trees as well as for interstems of apple trees.

5 Drawing Sheets

STATEMENT REGARDING FEDERAL FUNDING

Research related to this invention was funded under USDA ARS CRADA, Sponsor's Contract #: 58-3K95-9-1358-M; the U.S. government may have rights herein.

Genus and species: *Malus domestica×Malus robusta* hybrid.

Variety denomination: 'G.210'.

BACKGROUND OF THE INVENTION

I. Field & Utility Summary

The present invention relates to a new and distinct variety of apple tree rootstock. The rootstock is useful in that it can be propagated clonally and used as a rootstock or root system for apple trees as well as for interstems of apple trees.

II. Cultivation Summary

'G.210' rootstock originated from a planned cross in 1975 in Geneva, N.Y.

III. Characteristics Summary

The 'G.210' rootstock is a semi dwarfing rootstock that is resistant to fire blight (*Erwinia amylovora*) and crown rot (*Phytophthora cactorum*). While 'G.210' rootstock is a hybrid from a cross between 'Ottawa 3' and 'Robusta 5', it is distinct from its parent cultivars in terms of dwarfing. The apple tree rootstock 'G.210' is less dwarfing than 'Ottawa 3' and more dwarfing than the non-dwarfing parent 'Robusta 5'. Unlike 'Ottawa 3', 'G.210' is resistant to fire blight. Although 'G.210' is in the same dwarfing market class as 'Malling 7', it is distinguishable from 'Malling 7' because 'G.210' is precocious and highly productive whereas 'Malling 7' is less precocious and less productive.

IV. Breeding History

In the spring of 1975, pollen from a *Malus robusta* 'Robusta 5' apple tree was applied to emasculated flowers of a *Malus domestica* 'Ottawa 3' apple tree in Geneva, N.Y. In the fall of 1975, approximately 800 seeds resulting from this pollination were extracted from mature fruit derived from this cross. In the winter of 1975-76, the seeds were stratified and planted in large flats under conditions effective to germinate seeds and obtain seedlings. When germinated seedlings were about 2.5 cm tall they were inoculated with a mixture of isolates of the fungus *Phytophthora cactorum* (the causal agent of crown and root rots). The flats were flooded to mid-hypocotyl level and kept at 23° C. for one week. Surviving seedlings were transplanted into individual pots.

In the summer of 1976, each of the transplanted seedlings was inoculated with approximately $10^6$ colony forming units of the Ea 273 strain of the fire blight bacterium *Erwinia amylovora* by inserting a 26-gauge hypodermic syringe needle into the shoot tip. The seedling designated as #210 was one of the survivors of this battery of inoculations from the same cross. All the surviving plants were transplanted in Geneva, N.Y. in the fall of 1977 and allowed to grow side shoots for propagation/evaluation. In 1979, 'G.210' was evaluated for rooting ability, lack of spine production, and low root brittleness in a layering bed (stool bed). In 1983, 3 finished trees with 'G.210' rootstock were planted in Geneva, N.Y. with *Malus domestica* cv. 'Golden Delicious' grafted onto this rootstock as the scion cultivar. This rootstock performed well (top 20% of many rootstocks tested) in these first test trials. In August of 2002, several rootstock liners of 'G.210' were budded with 15 different scion cultivars to test graft union compatibility—the test results showed that 'G.210' was compatible with all the cultivars tested. In the summer of 2002, 40 rootstock liners were inoculated with four different strains of fire blight (ten liners per strain) in Geneva, N.Y. As a result, the apple rootstock 'G.210' was classified as immune to two of the strains tested and moderately resistant to the other two strains of fire blight. During the 2003-2005 seasons, field observations were made on the stool bed plants and roots of 'G.210' for the presence of wooly apple aphids (*Eriosoma lanigerum*) and was found to be free of wooly apple aphids whereas other rootstock plants in the same field plot were found to be infested. In the 2006 growing season, comparative data with other field grown rootstocks on the Loomis Farm was taken for presence of symptoms (sporulation) of powdery mildew fungus on leaves (*Podosphaera leucotricha*) and 'G.210' exhibited resistance to the fungus. In addition a molecular marker assay was conducted on 'G.210' for the presence of the resistance gene to powdery mildew derived from 'Robusta 5' and marker E62M40_266 was found to be present in 'G.210'.

V. Asexual Reproduction

Asexual reproduction of the 'G.210' apple rootstock has been achieved using the traditional method of clonally propagating apple rootstocks. In particular, the original seedling of the 'G.210' apple rootstock was planted in Geneva, N.Y. and allowed to develop into a "mother plant." The 'G.210' mother plant was then used to obtain rooted liners using conventional layering procedures. The resulting liners were then planted in a row to generate a layering stool bed (also referred to as the "mother stool bed"). The living tissues (i.e. leaves, stems, roots, buds, and spines) of the mother stool bed were observed to be identical to secondary and tertiary stool bed plants. In addition to conventional layering, the 'G.210' apple rootstock variety has been asexually reproduced by root cuttings, by budding and grafting onto seedling and clonal rootstocks, and by tissue culture.

VI. Stability

Observations of trees from these propagations indicate that all trees have been proven true to type and identical in all appearances to the original tree.

VII. Detailed Comparisons

The seed parent *Malus domestica* 'Ottawa 3' is a dwarfing rootstock, i.e., trees grown on this rootstock are 30 to 35 percent the size of a standard self-rooted seedling tree. 'Ottawa 3' is known to induce good precocity to the scion (i.e., the ability to induce early reproductive development in the scion) and has high yield efficiency. 'Ottawa 3' plants produce no spines, are fairly well anchored, are a very cold hardy rootstock and have resistance to crown and root rot caused by *Phytophthora cactorum*. However, 'Ottawa 3' is susceptible to the woolly apple aphid (*Eriosoma lanigerum*) and to fire blight (*Erwinia amylovora*).

The pollen parent *Malus robusta* 'Robusta 5' is a non-dwarfing rootstock, i.e. trees on this rootstock are the same size as a standard self-rooted tree. 'Robusta 5' does not induce precocity to the scion and is not highly yield efficient. Juvenile plants of 'Robusta 5' produce many spines. 'Robusta 5' breaks buds very early in the spring and is winter hardy. It is resistant to powdery mildew (*Podosphaera leucotricha*) and fire blight, and is immune to the woolly apple aphid. Further, 'Robusta 5' has shown tolerance to the specific replant disease complex.

The 'G.210' apple rootstock of the present invention has a combination of qualities that distinguishes it from its parental plants (i.e., 'Ottawa 3' and 'Robusta 5'). For example, although 'G.210' has dwarfing properties derived from 'Ottawa 3', it is different from its dwarfing parent (i.e., 'Ottawa 3') because it produces a tree that is 50 to 60 percent of the size of a standard self-rooted seedling tree. Thus 'G.210' belongs to a different dwarfing vigor class than its 'Ottawa 3' parent. In particular, 'G.210' has dwarfing characteristics that are similar to the industry standard of *Malus domestica* 'Malling 7'. 'G.210' shares similarities with 'Ottawa 3' in that they both induce precocity to the scion, are highly yield efficient, winter hardy, and fairly well anchored.

With regard to its 'Robusta 5' parent, 'G.210' is distinguishable in that it is a dwarfing rootstock and is highly yield efficient, while 'Robusta 5' is not. However, like 'Robusta 5', 'G.210' is resistant to fire blight, powdery mildew, and the woolly apple aphid (*Eriosoma lanigerum*). In addition, 'G.210' has been shown to have some tolerance to the replant disease complex.

As discussed above, 'G.210' is most similar to 'Malling 7' in terms of dwarfing class. However, 'G.210' is more precocious and yield efficient than 'Malling 7'.

With regard to apple tree rootstock 'G.969', a variety from the same parents as 'G.210', 'G.210' produced trees that were at approximately 10 to 15% more vigorous than 'G.969', when grown in the northeast United States. 'G.969' showed higher cumulative yield efficiency than 'G.210', when grown in the northeast United States. 'G.210' is more efficient at absorbing and translocating sodium to the scion leaves than 'G.969'.

With regard to apple tree rootstock 'G.935', a variety from the same parents as 'G.210', 'G.210' produced trees that were approximately 15 to 25% more vigorous than 'G.935' when grown in the northeast United States, placing 'G.210' in a different dwarfing category than 'G.935'. G.210 is resistant to wooly apple aphid (*Eriosoma lanigerum*) and 'G.935' is susceptible. 'G.210' has straighter leaves with wavy edges, while 'G.935' has epinastic recurved leaves.

DETAILED BOTANICAL DESCRIPTION

Figure 1:
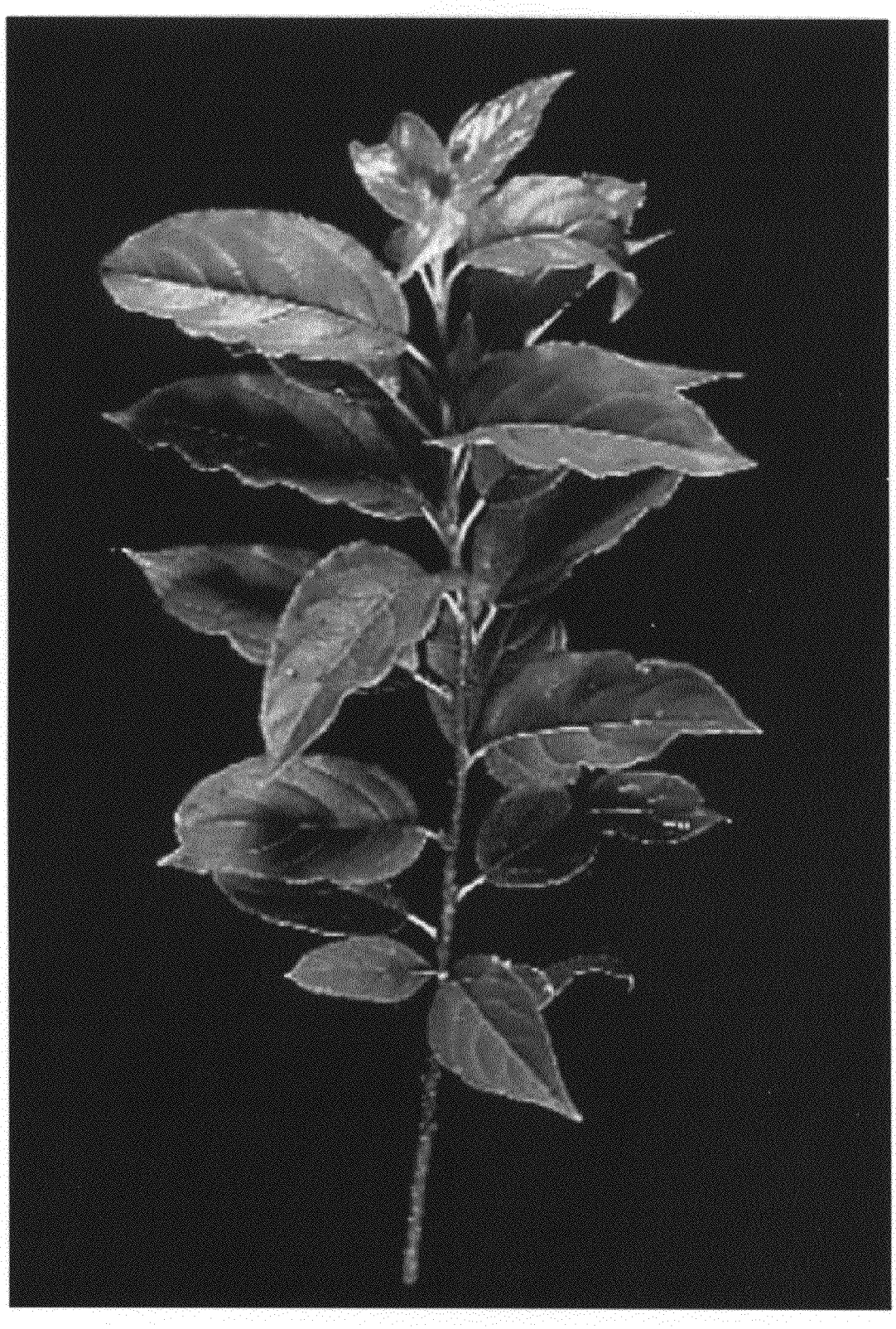
FIG. 1 shows a shoot (including leaves and bark). The shoot shown is a fresh shoot, and is less than one year old.
Figure 2:
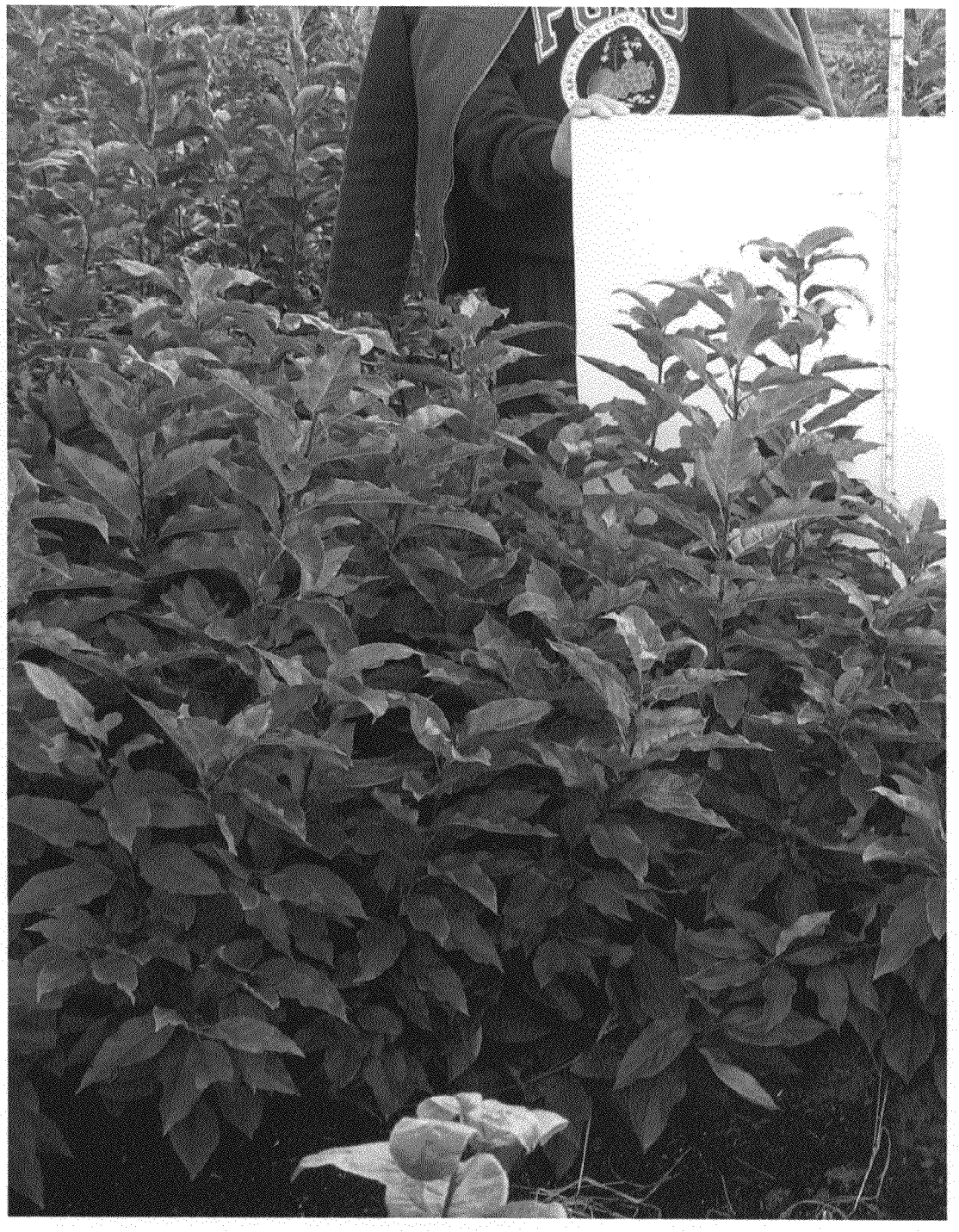
FIG. 2 shows growing shoots in a stool bed. The shoots shown are one year old, and grown from a stoolbed that is more than ten years old.
Figure 3:
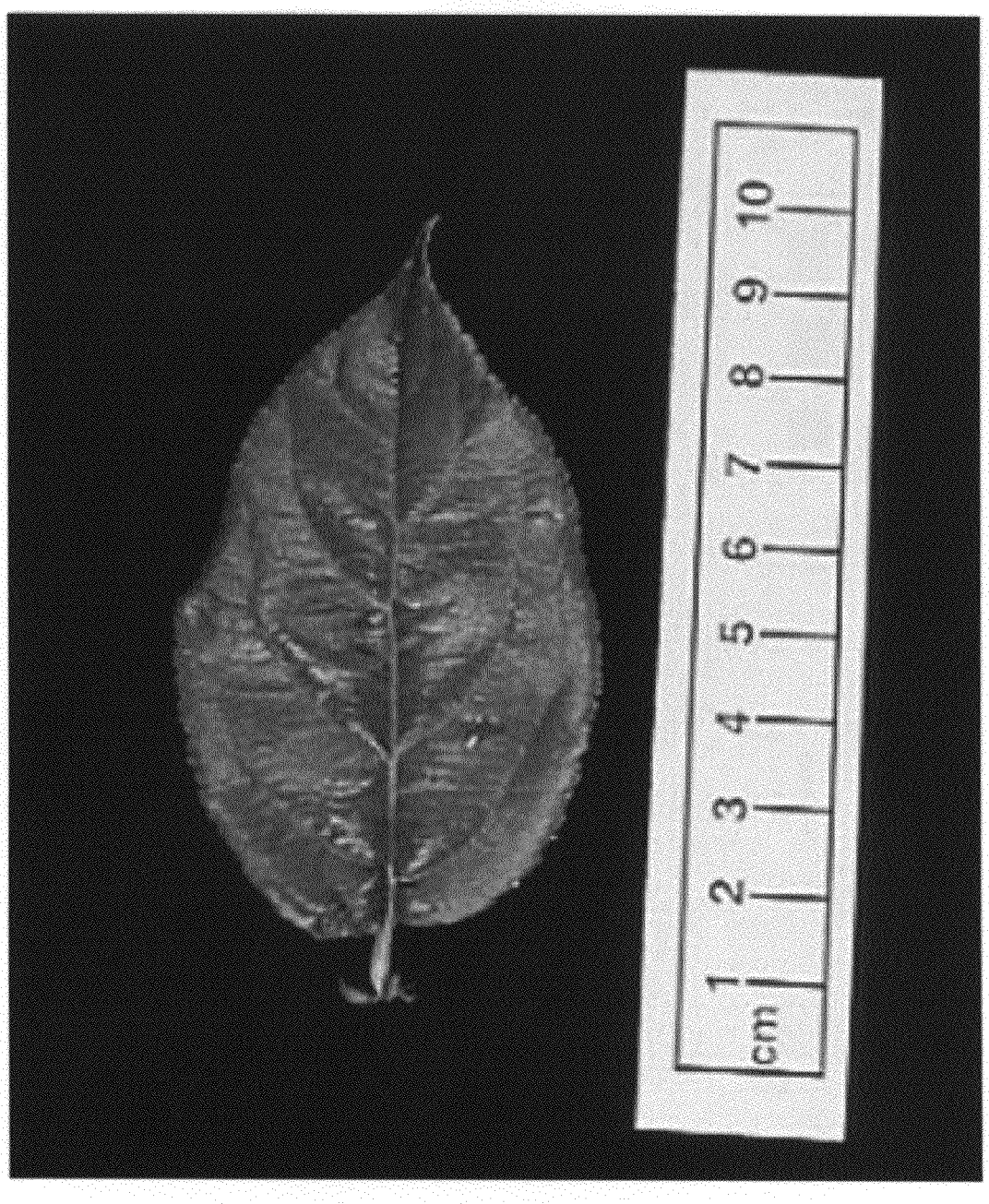
FIG. 3 shows the adaxial (upper) lamina surface of a mature leaf. The leaf shown is from a one season old plant.
Figure 4:
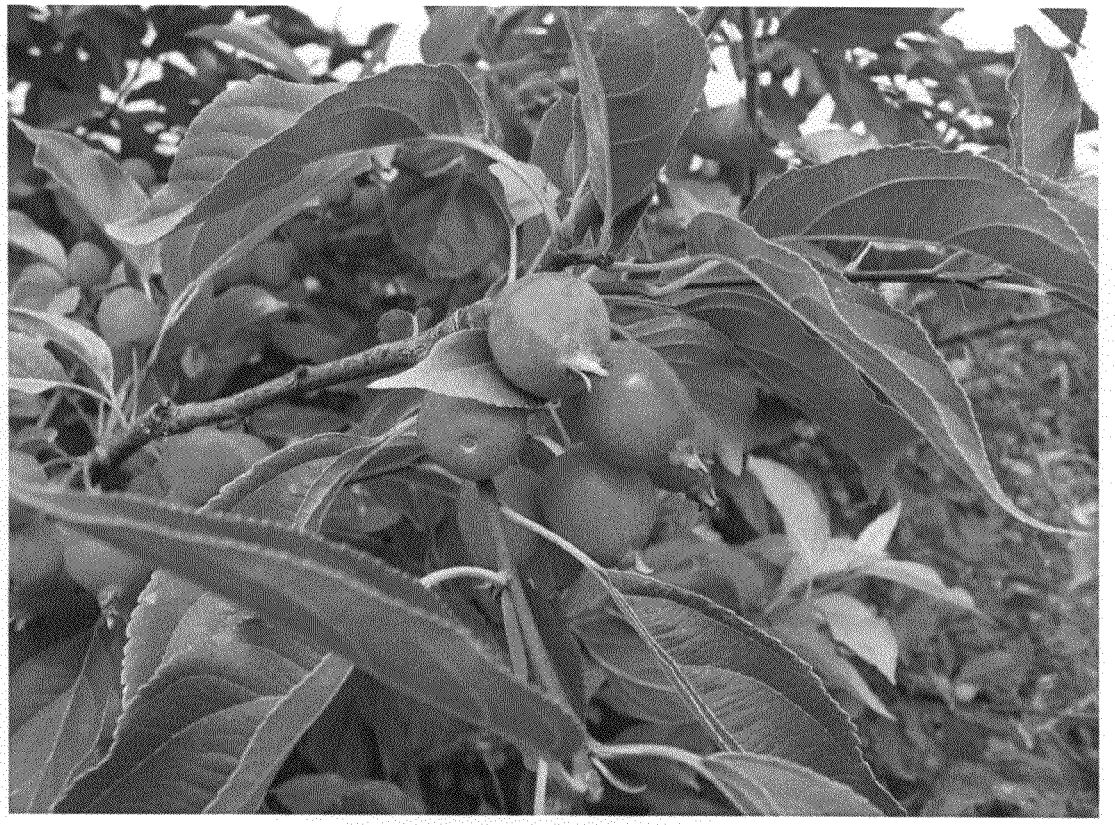
FIG. 4 shows bark, mature leaves and fruit. The bark, mature leaves, and fruit shown is from a seven year old plant, with the shoots at the base of the tree being a variety of seasons old.
Figure 5:
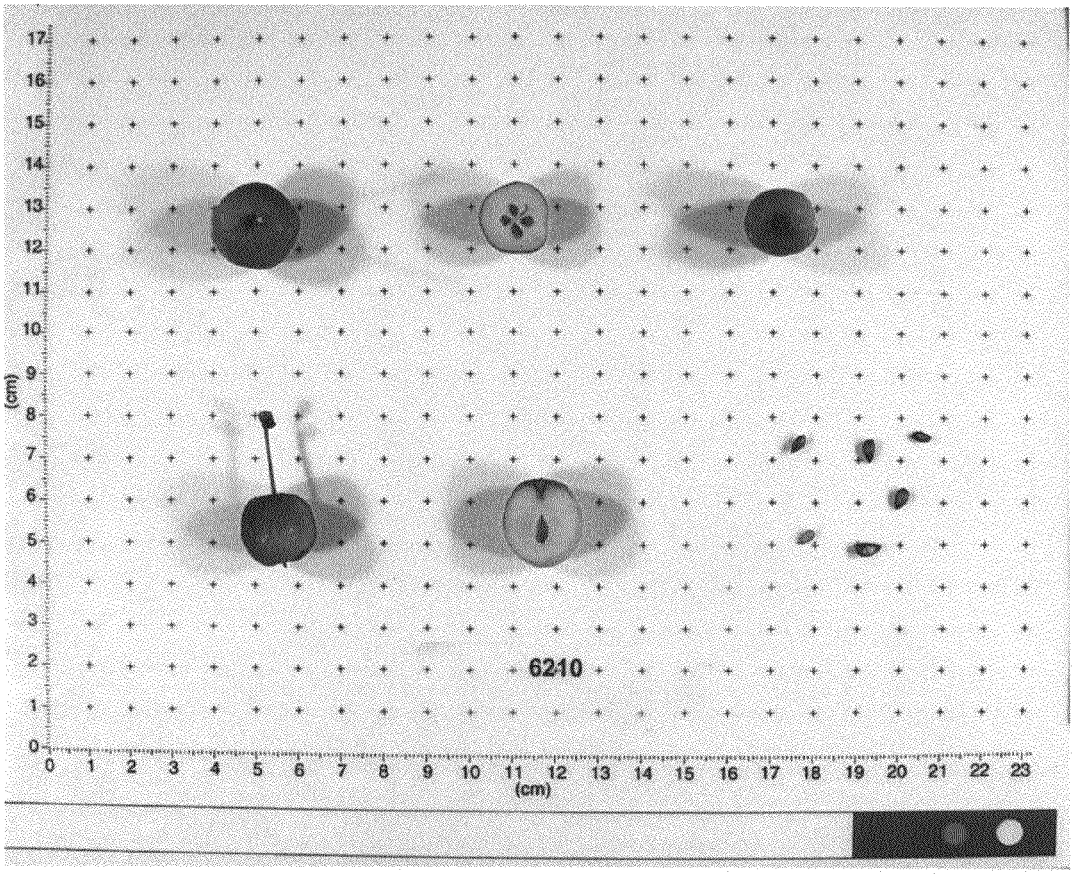
FIG. 5 shows the mature fruit. The fruit show is from a seven year old plant.

The following description of apple tree rootstock 'G.210' contains references to color names taken from The Royal Horticultural Society Colour Chart (R.H.S.), 2001 edition. Botanical descriptions follow the Manual of Cultivated Plants (Bailey, 1949).

Tree:

*Habit*.—A self-rooted tree of 'G.210' is a small shrub typically standing about 1.5-2 meters tall by about 2 meters wide when 7 years old. There is no single dominant trunk. Instead there are few shoots arising from the crown. Very few suckers (i.e., new shoots emerging from below ground) are produced. Liners planted in the nursery stop apical growth mid season. The apical bud in these plants is pubescent Greyed-Green (RHS 191D).

*Productivity*.—In an intermediate trial performed in Geneva, N.Y. the 'G.210' rootstock received the cultivar 'Empire' (*Malus domestica*) as the scion and was compared to the *Malus domestica* check rootstocks M.9 EMLA, M.26 and M.7. 'G.210' was shown to have statistically higher ($p \leqq 0.05$) yield efficiency (kg yield/$cm^2$ trunk cross sectional area) than all the check rootstocks.

*Precocity*.—Scion cultivars budded on 'G.210' exhibit the same precocity as those budded on M.26.

*Fertility* (*fecundity*).—The 'G.210' plant produces flowers and fruits regularly.

Dormant shoots (buds and bark):

*Dormant mature shoots*.—Color: Greyed-Red (RHS 178A) where exposed to full sunlight grading to Greyed-Orange (RHS 173B) with diminished light exposure. Texture: Very light pubescence which gradually disappears in older tissues. Size: 30-60 cm long; may have some spines.

*Axillary buds*.—Size: 2-3 mm long and 3 mm wide with little pubescence. Shape: Obtuse, sessile, somewhat appressed and flattened. Texture: Some pubescence.

*Bark on three-year-old shoots*.—Color: Greyed-Green (RHS 197A). Lenticels: Color: Greyed-Orange (RHS 163B). Size: 0.3-0.4 mm in diameter. Quantity: 1-2 lenticels per $cm^2$.

Leaves:

*Mature leaves*.—Leaf arrangement: Alternate. Shape: Simple, recurved, oblong-ovate. Size: Length: 85 mm. Width: 50 mm at the widest point. Laminae: Wavy edges. Apex: Acuminate. Base: Nearly symmetrical rounded. Margin: Acutely serrated, with about 5 serrations per cm. Upper surface: Color: Green (RHS 126B). Texture: Glabrous and translucent. Lower surface: Color: Green (RHS 146C). Texture: Somewhat pubescent. Venation: Netted. Leaf poise: 15°-25° from the shoot, depending on shoot orientation. Stipules: Length: 8 mm. Width: 2 mm. Petioles: Diameter: 2 mm. Color: Gradation of Green (RHS 140A) to Greyed-Red (RHS 179A) depending on low or high exposure to light.

Flowers:

*Habit*.—Flowers borne on spurs, shoot terminals, and from lateral buds on growth from previous season.

*Flower diameter*.—40 mm.

*Fragrance*.—None.

*Buds*.—Location: Located on spurs and terminals; are mixed, typically producing a truss of 5 to 6 flowers and one bourse shoot. Shape: Lateral buds are obtuse, sessile and somewhat appressed. Size: Length: 4 mm. Width: 3 mm. Habit: Buds near the base of the shoot of the previous season usually produce 3 to 5 flowers and a single short shoot; mid-shoot buds may have 2-4 flowers; and more distal buds are usually vegetative.

*Petals*.—Size: Length: 25 mm. Width: 18 mm. Shape: Spatulate. Apex: Obtuse. Margin: Smooth. Texture: Smooth. Color: Closed petals: Red (RHS 54A). Open petals: White (RHS 155D) with Red (RHS 54A) striations in some of the petals.

*Reproductive organs*.—Pistils: Length: 6 mm. Color: Yellow-white (RHS 145B). Stamens: Length: 4 mm. Color: White (RHS 155D). Anther color: Yellow-Brown (RHS 167D).

Fruit:

*Mature fruit*.—Size: Height: 30-35 mm. Diameter: 30-35 mm. Shape: Round Obloid. Color: Partial Red-skin (RHS 46C) with Red (RHS 42B) blush undertones depending on the exposure to the sun. Sepals: Sometimes persisting on a variable protruding calyx. Flesh: Taste: Astringent (not meant for consumption). Color: Yellow-Orange (RHS 17C) with Red (RHS 42B) bleed through from the skin in mature fruits. Seed: Color: Greyed-Red (RHS 178A), translucent. Shape: Tear drop shape. Size: Length: 50-60 mm. Diameter: 25-35 mm at the widest point. Number: Generally five seed per fruit.

Disease resistance: As described above, the 'G.210' rootstock of the present invention exhibits resistance to fire blight. The percent lesion measured after inoculation of potted liners in the greenhouse using four different strains of *E. amylovora* was negligible for two of the strains and moderate for the other two, indicating a specific resistance to the bacterium. The 'G.210' rootstock, having survived the inoculation with crown and root rot, is also considered resistant to crown and root rots caused by *Phytophthora cactorum*.

We claim:

1. A new and distinct variety of apple rootstock named 'G.210' herein described and illustrated.

* * * * *